United States Patent
Goto et al.

(10) Patent No.: US 11,406,333 B2
(45) Date of Patent: Aug. 9, 2022

(54) MEDICAL IMAGE DIAGNOSIS APPARATUS AND MANAGEMENT APPARATUS

(71) Applicant: Toshiba Medical Systems Corporation, Otawara (JP)

(72) Inventors: Takahiro Goto, Utsunomiya (JP); Shinsuke Tsukagoshi, Nasushiobara (JP); Go Mukumoto, Obu (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 421 days.

(21) Appl. No.: 15/590,632

(22) Filed: May 9, 2017

(65) Prior Publication Data
US 2017/0319150 A1 Nov. 9, 2017

(30) Foreign Application Priority Data

May 9, 2016 (JP) .............................. JP2016-094099
May 1, 2017 (JP) .............................. JP2017-091270

(51) Int. Cl.
*A61B 6/00* (2006.01)
*G16H 20/17* (2018.01)
(Continued)

(52) U.S. Cl.
CPC ............ *A61B 6/032* (2013.01); *A61B 6/4035* (2013.01); *A61B 6/465* (2013.01); *A61B 6/481* (2013.01);
(Continued)

(58) Field of Classification Search
CPC .................................................. A61M 5/007
See application file for complete search history.

(56) References Cited

U.S. PATENT DOCUMENTS 5,840,026 A * 11/1998 Uber, III .................. A61B 8/06
   600/431
6,246,745 B1 * 6/2001 Bi .......................... A61B 6/505
   378/54
(Continued)

FOREIGN PATENT DOCUMENTS

JP 2008-12171 1/2008
JP 2008-12229 1/2008
(Continued)

OTHER PUBLICATIONS

Weininger et al. Cardiothoracic CT Angiography: Current Contrast Medium Delivery Strategies. AJR 2011; 196:W260-W272 (Year: 2011).*
(Continued)

*Primary Examiner* — Angela M Hoffa
*Assistant Examiner* — Younhee Choi
(74) *Attorney, Agent, or Firm* — Oblon, McClelland, Maier & Neustadt, L.L.P.

(57) ABSTRACT

A medical image diagnosis apparatus according to an embodiment includes obtaining circuitry, detecting circuitry, deriving circuitry, and controlling circuitry. The obtaining circuitry is configured to obtain image data of a patient. The detecting circuitry is configured to detect each of a plurality of sites of the patient from the image data. The deriving circuitry is configured to derive information about a structuring member in the patient, on the basis of a detection result obtained by the detecting circuitry. The controlling circuitry is configured to determine an injection condition for a contrast agent to be administered to the patient for a contrast-enhanced scan, on the basis of the information about the structuring member.

14 Claims, 12 Drawing Sheets

| SKELETON MASS | MUSCLE MASS | SIZE OF ORGAN | AMOUNT OF CONTRAST AGENT TO BE ADMINISTERED |
|---|---|---|---|
| 1.10Y (ml) | 0.90Y (ml) | 0.90Y (ml) | 0.97Y (ml) |

(51) Int. Cl.
  *A61B 6/03* (2006.01)
  *G16H 30/40* (2018.01)
  *A61B 6/06* (2006.01)

(52) U.S. Cl.
  CPC .............. *A61B 6/488* (2013.01); *A61B 6/504* (2013.01); *A61B 6/5205* (2013.01); *A61B 6/5294* (2013.01); *A61B 6/545* (2013.01); *G16H 20/17* (2018.01); *G16H 30/40* (2018.01); *A61B 6/06* (2013.01)

(56) References Cited

U.S. PATENT DOCUMENTS

| | | | | |
|---|---|---|---|---|
| 7,289,841 | B2* | 10/2007 | Johnson | A61B 5/02014 600/407 |
| 8,086,012 | B2* | 12/2011 | Toth | A61B 5/411 378/4 |
| 2010/0098310 | A1* | 4/2010 | Toth | G06T 7/0012 382/131 |
| 2010/0113887 | A1* | 5/2010 | Kalafut | A61B 8/481 600/300 |
| 2010/0183206 | A1* | 7/2010 | Carlsen | A61B 6/488 382/128 |
| 2012/0236995 | A1* | 9/2012 | Eusemann | A61B 6/481 378/108 |
| 2013/0190592 | A1* | 7/2013 | Coppini | G06T 11/003 600/407 |
| 2015/0262358 | A1* | 9/2015 | Schormans | G06T 7/0016 382/103 |
| 2016/0213833 | A1* | 7/2016 | Coudyzer | A61M 5/16877 |
| 2017/0316562 | A1* | 11/2017 | Haberland | G06T 7/0012 |
| 2018/0242917 | A1* | 8/2018 | Bagherzadeh | A61B 5/7221 |

FOREIGN PATENT DOCUMENTS

| | | |
|---|---|---|
| JP | 2012-232029 | 11/2012 |
| JP | 2014-14715 | 1/2014 |
| JP | 2016-531708 A | 10/2016 |
| WO | WO 2008/081830 A1 | 7/2008 |
| WO | WO 2008/126417 A1 | 10/2008 |

OTHER PUBLICATIONS

Japanese Office Action dated Mar. 9, 2021, issued in Japanese Patent Application No. 2017-091270.

* cited by examiner

FIG.3
HELICAL SCAN
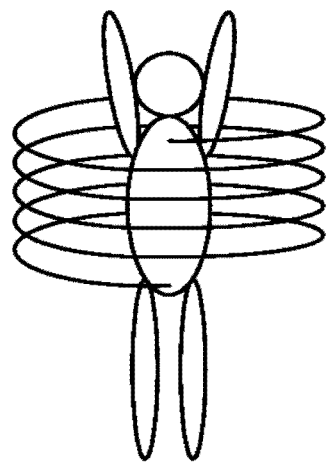
or
NON-HELICAL SCAN
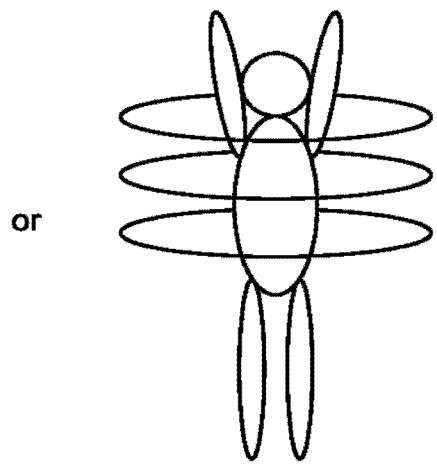
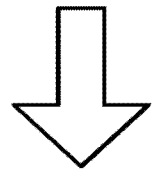
VOLUME DATA
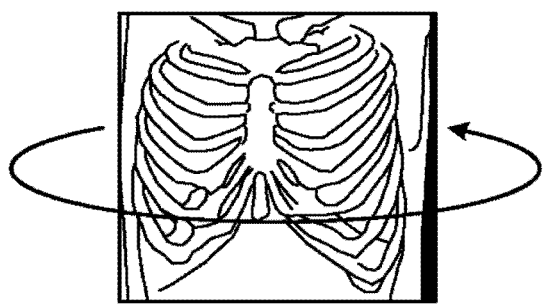
GENERATE POSITION
DETERMINING IMAGE
FROM ARBITRARY
DIRECTION

FIG.5

| IDENTIFICATION CODE | COORDINATES | | |
|---|---|---|---|
| | POSITION DETERMINING | SCANS | |
| | | NON-CONTRAST-ENHANCED PHASE | CONTRAST-ENHANCED PHASE |
| C1 | (x1, y1, z1) | (x'1, y'1, z'1) | (x'1, y'1, z'1) |
| C2 | (x2, y2, z2) | (x'2, y'2, z'2) | (x'2, y'2, z'2) |
| C3 | (x3, y3, z3) | (x'3, y'3, z'3) | (x'3, y'3, z'3) |
| C4 | (x4, y4, z4) | (x'4, y'4, z'4) | (x'4, y'4, z'4) |
| C5 | (x5, y5, z5) | (x'5, y'5, z'5) | (x'5, y'5, z'5) |
| C6 | (x6, y6, z6) | (x'6, y'6, z'6) | (x'6, y'6, z'6) |
| C7 | (x7, y7, z7) | (x'7, y'7, z'7) | (x'7, y'7, z'7) |
| C8 | (x8, y8, z8) | (x'8, y'8, z'8) | (x'8, y'8, z'8) |
| C9 | (x9, y9, z9) | (x'9, y'9, z'9) | (x'9, y'9, z'9) |
| C10 | (x10, y10, z10) | (x'10, y'10, z'10) | (x'10, y'10, z'10) |
| ⋮ | ⋮ | ⋮ | ⋮ |
| C31 | | | (x'31, y'31, z'31) |
| C32 | | | (x'32, y'32, z'32) |
| C33 | | | (x'33, y'33, z'33) |
| C34 | | | (x'34, y'34, z'34) |
| ⋮ | ⋮ | ⋮ | ⋮ |

FIG.10

| TYPES OF ORGAN | SIZES OF ORGAN | AMOUNTS OF CONTRAST AGENT |
|---|---|---|
| ... | ... | ... |
| LIVER | X1 TO X2 | 0.90Y (ml) |
| LIVER | X2 TO X3 | 0.95Y (ml) |
| LIVER | X3 TO X4 | Y (ml) |
| LIVER | X4 TO X5 | 1.05Y (ml) |
| LIVER | X5 TO X6 | 1.10Y (ml) |
| ... | ... | ... |

FIG.12

| SKELETON MASS | MUSCLE MASS | SIZE OF ORGAN | AMOUNT OF CONTRAST AGENT TO BE ADMINISTERED |
|---|---|---|---|
| 1.10Y (ml) | 0.90Y (ml) | 0.90Y (ml) | 0.97Y (ml) |

FIG.13

<CAUTION>
PATIENT IS ALLERGIC
TO CONTRAST AGENTS.

MEDICAL IMAGE DIAGNOSIS APPARATUS AND MANAGEMENT APPARATUS

CROSS-REFERENCE TO RELATED APPLICATIONS

This application is based upon and claims the benefit of priority from Japanese Patent Application No. 2016-094099, filed on May 9, 2016 and Japanese Patent Application No. 2017-091270, filed on May 1, 2017; the entire contents of which are incorporated herein by reference.

FIELD

Embodiments described herein relate generally to a medical image diagnosis apparatus and a management apparatus.

BACKGROUND

Conventionally, during a medical examination using an X-ray Computed Tomography (CT) apparatus, in some situations, a contrast-enhanced scan may be performed by administering a contrast agent to the examined subject (hereinafter "patient"). In those situations, the X-ray CT apparatus determines an injection condition for a contrast agent to be administered to the patient, on the basis of the height, the weight, a Body Mass Index (BMI) and/or the like of the patient.

BRIEF DESCRIPTION OF THE DRAWINGS

FIG. 3 is a drawing for explaining a three-dimensional scanogram image taking process performed by scan controlling circuitry according to the first embodiment;

FIG. 5 is a table for explaining the example of the site detecting process performed by the detecting function according to the first embodiment;

FIG. 10 is a drawing for explaining the first embodiment;

FIG. 12 is a drawing for explaining a second embodiment; and

FIG. 13 is a drawing for explaining another embodiment.

DETAILED DESCRIPTION

Exemplary embodiments of a medical image diagnosis apparatus and a management apparatus will be explained in detail below, with reference to the accompanying drawings. In the following sections, a medical information processing system including an X-ray Computed Tomography (CT) apparatus will be explained as an example. In a medical information processing system 100 in FIG. 1, only one server apparatus and one terminal apparatus are illustrated; however, in actuality, the system may include two or more server apparatuses and/or two or more terminal apparatuses. Further, for example, the medical information processing system 100 may also include one or more medical image diagnosis apparatuses such as X-ray diagnosis apparatuses, Magnetic Resonance Imaging (MRI) apparatuses, ultrasound diagnosis apparatuses, and/or the like.

First Embodiment

Figure 1:
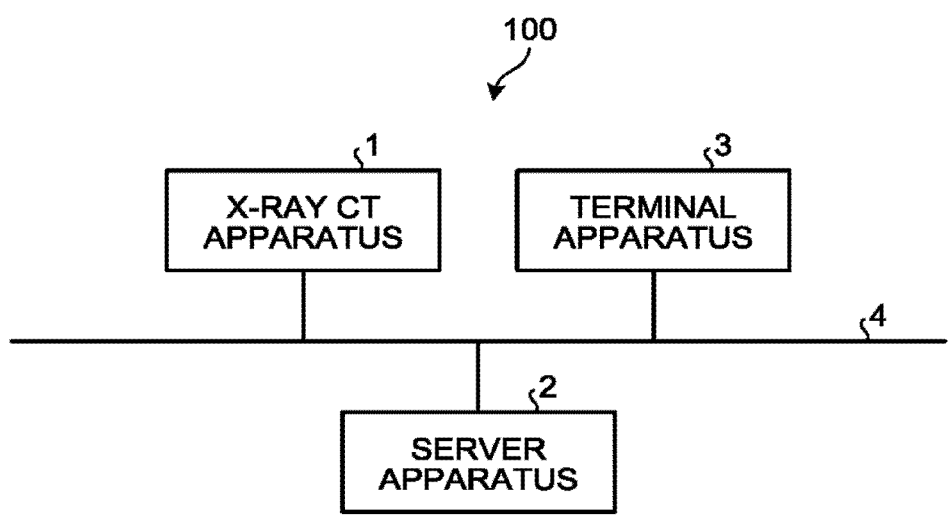
FIG. 1 is a diagram illustrating an exemplary configuration of a medical information processing system according to a first embodiment.

FIG. 1 is a diagram illustrating an exemplary configuration of the medical information processing system 100 according to a first embodiment. As illustrated in FIG. 1, the medical information processing system 100 according to the first embodiment includes an X-ray CT apparatus 1, a server apparatus 2, and a terminal apparatus 3. The X-ray CT apparatus 1, the server apparatus 2, and the terminal apparatus 3 are in a state of being able to communicate with one another either directly or indirectly via, for example, an intra-hospital Local Area Network (LAN) installed in a hospital. For example, when a Picture Archiving and Communication System (PACS) is introduced into the medical information processing system 100, the apparatuses are configured to transmit and receive medical images and the like to and from one another according to the Digital Imaging and Communication in Medicine (DICOM) standard.

Further, a Hospital Information System (HIS) or a Radiology Information System (RIS), for example, is introduced into the medical information processing system 100 so as to manage various types of information. For example, the terminal apparatus 3 transmits a medical examination order generated in accordance with the system described above, to the X-ray CT apparatus 1 and to the server apparatus 2. The X-ray CT apparatus 1 obtains patient information either from the medical examination order directly received from the terminal apparatus 3 or from a patient list (a modality work list) generated in correspondence with each modality by the server apparatus 2 that received the medical examination order. The X-ray CT apparatus 1 further acquires X-ray CT image data for each patient. After that, the X-ray CT apparatus 1 transmits the acquired X-ray CT image data and image data generated by performing any of various types of image processing processes on the X-ray CT image data, to the server apparatus 2. The server apparatus 2 stores therein the X-ray CT image data and the image data received from the X-ray CT apparatus 1, and also, generates image data from the X-ray CT image data, and transmits any of the image data to the terminal apparatus 3 in response to an obtainment request from the terminal apparatus 3. The terminal apparatus 3 displays the image data received from the server apparatus 2 on a monitor or the like. The following sections describe each of the apparatuses.

The terminal apparatus 3 is an apparatus provided in each medical department in the hospital and is operated by medical doctors working in various medical departments. The terminal apparatus 3 may be a Personal Computer (PC) a tablet-type PC, a Personal Digital Assistant (PDA), a mobile phone, or the like. For example, to the terminal apparatus 3, medical doctors input medical chart information including patients' symptoms and medical doctors' observations. Further, to the terminal apparatus 3, a medical examination order to order a medical examination using the X-ray CT apparatus 1 is input. The terminal apparatus 3 transmits the input medical examination order to the X-ray CT apparatus 1 and to the server apparatus 2. In other words, each of the medical doctors working in the medical departments operates the terminal apparatus 3 so as to read reception information and electronic chart information of each patient who came to the hospital, gives a consultation to his/her patients, and inputs medical chart information to a read electronic chart. After that, each of the medical doctors working in the medical departments transmits a medical examination order by operating the terminal apparatus 3, depending on whether or not a medical examination using the X-ray CT apparatus 1 is required.

The server apparatus 2 is an apparatus configured to store therein medical images acquired by a medical image diagnosis apparatus (e.g., the X-ray CT image data and the image data acquired by the X-ray CT apparatus 1) and to perform various types of image processing processes on the medical images. For example, the server apparatus 2 may be configured by using a PACS server. For example, the server apparatus 2 is configured to receive a plurality of medical examination orders from the terminal apparatus 3 provided in each of the medical departments, to generate a patient list for each medical image diagnosis apparatus, and to transmit each of the generated patient lists to a corresponding one of the medical image diagnosis apparatuses. In one example, the server apparatus 2 receives medical examination orders for performing medical examinations by using the X-ray CT apparatus 1 from the terminal apparatus 3 provided in each medical department, generates patient lists, and transmits the generated patient lists to the X-ray CT apparatus 1. After that, the server apparatus 2 stores therein the X-ray CT image data and the image data acquired by the X-ray CT apparatus 1 and further transmits the X-ray CT image data and the image data to the terminal apparatus 3, in response to an obtainment request from the terminal apparatus 3.

Figure 2:
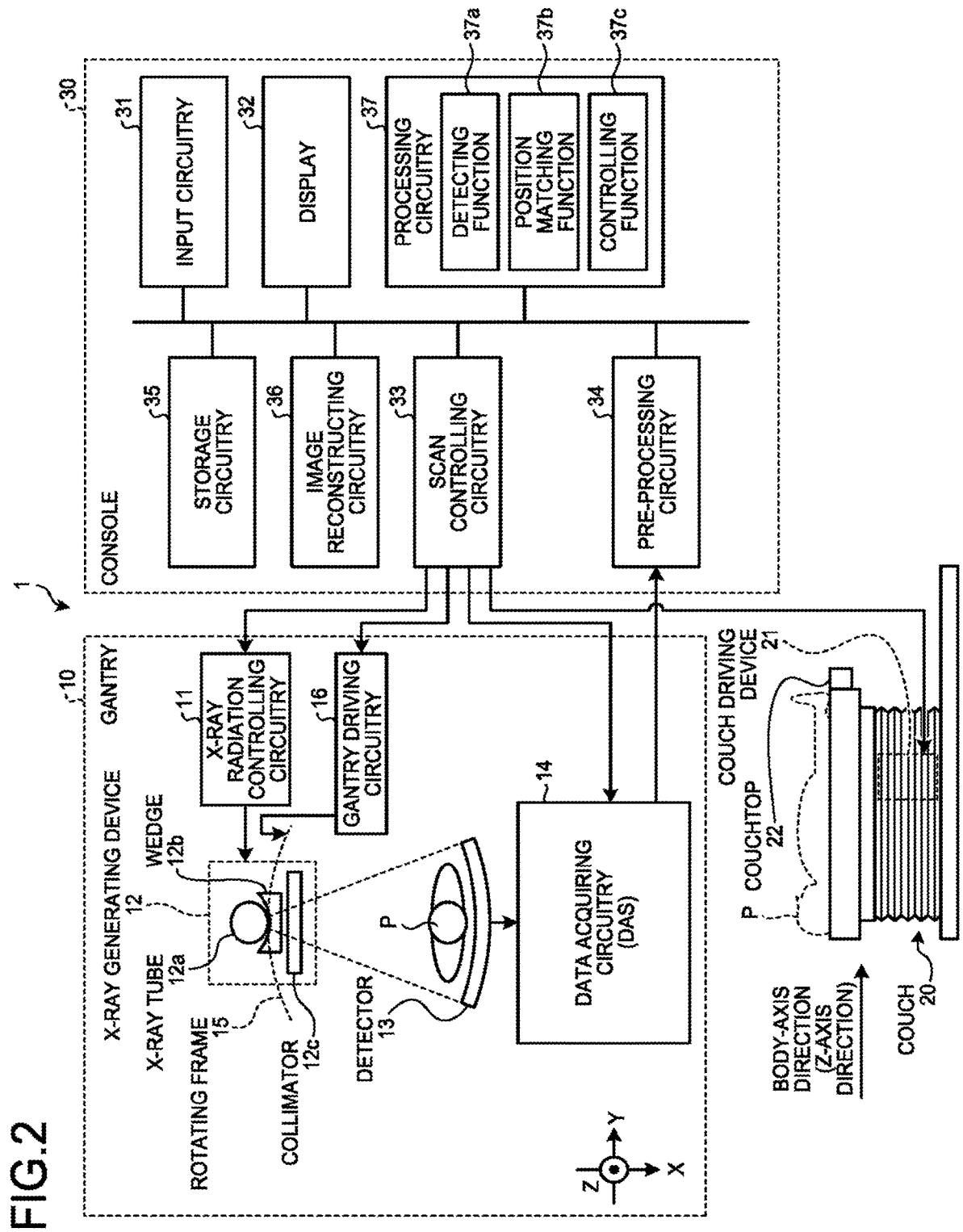
FIG. 2 is a diagram illustrating an exemplary configuration of an X-ray CT apparatus according to the first embodiment.

The X-ray CT apparatus 1 is configured to acquire the X-ray CT image data from each patient and to transmit the acquired X-ray CT image data and the image data generated by performing any of the various types of image processing processes on the X-ray CT image data, to the server apparatus 2. FIG. 2 is a diagram illustrating an exemplary configuration of the X-ray CT apparatus 1 according to the first embodiment. As illustrated in FIG. 2, the X-ray CT apparatus 1 according to the first embodiment includes a gantry 10, a couch 20, and a console 30. Further, the X-ray CT apparatus 1 is connected to a contrast agent injector (not illustrated in FIG. 2).

The gantry 10 is a device configured to radiate X-rays onto an examined subject P (the patient), to detect X-rays that have passed through the patient P, and to output a result of the detection to the console 30. The gantry 10 includes X-ray radiation controlling circuitry 11, an X-ray generating device 12, a detector 13, and data acquiring circuitry (a Data Acquisition System [DAS]) 14, a rotating frame 15, and gantry driving circuitry 16. The data acquiring circuitry 14 is an example of obtaining circuitry.

The rotating frame 15 is an annular frame configured to support the X-ray generating device 12 and the detector 13 so as to oppose each other while the patient P is interposed therebetween and configured to be rotated by the gantry driving circuitry 16 (explained later) at a high speed on a circular orbit centered on the patient P.

The X-ray radiation controlling circuitry 11 is a device configured, as a high-voltage generating unit, to supply a high voltage to an X-ray tube 12a. The X-ray tube 12a is configured to generate X-rays by using the high voltage supplied thereto from the X-ray radiation controlling circuitry 11. The X-ray radiation controlling circuitry 11 is configured to adjust the X-ray dose radiated onto the patient P, by adjusting the X-ray tube voltage and the X-ray tube current supplied to the X-ray tube 12a, under control of scan controlling circuitry 33 (explained later).

Further, the X-ray radiation controlling circuitry 11 is configured to perform a switching process on a wedge 12b. Further, by adjusting the opening degree of a collimator 12c, the X-ray radiation controlling circuitry 11 is configured to adjust the radiation range (a fan angle or a cone angle) of the X-rays. In the present embodiments, an arrangement is acceptable in which an operator manually switches among a plurality of types of wedges.

The X-ray generating device 12 is a device configured to generate the X-rays and to radiate the generated X-rays onto the patient P. The X-ray generating device 12 includes the X-ray tube 12a, the wedge 12b, and the collimator 12c.

The X-ray tube 12a is a vacuum tube configured to radiate an X-ray beam onto the patient P by using the high voltage supplied thereto by the high-voltage generating unit (not illustrated). The X-ray tube 12a radiates the X-ray beam onto the patient P, as the rotating frame 15 rotates. The X-ray tube 12a is configured to generate the X-ray beam that spreads with the fan angle or the cone angle. For example, under the control of the X-ray radiation controlling circuitry 11, the X-ray tube 12a is capable of continuously emitting X-rays in the entire surrounding of the patient P to realize a full reconstruction process and is capable of continuously emitting X-rays in an emission range (180 degrees+the fan angle) that enables a half reconstruction to realize a half reconstruction process. Further, under the control of the X-ray radiation controlling circuitry 11, the X-ray tube 12a is capable of intermittently emitting X-rays (pulse X-rays) in positions (X-ray tube positions) set in advance. Further, the X-ray radiation controlling circuitry 11 is also capable of modulating the intensities of the X-rays emitted from the X-ray tube 12a. For example, the X-ray radiation controlling circuitry 11 increases the intensities of the X-rays emitted from the X-ray tube 12a in a specific X-ray tube position and decreases the intensities of the X-rays emitted from the X-ray tube 12a in a range other than the specific X-ray tube position.

The wedge 12b is an X-ray filter configured to adjust the X-ray dose of the X-rays emitted from the X-ray tube 12a. More specifically, the wedge 12b is a filter configured to pass and attenuate the X-rays emitted from the X-ray tube 12a, so that the X-rays radiated from the X-ray tube 12a onto the patient P have a predetermined distribution. For example, the wedge 12b is a filter obtained by processing aluminum so as to have a predetermined target angle and a predetermined thickness. The wedge may be referred to as a wedge filter or a bow-tie filter.

The collimator 12c is a slit configured to narrow down the radiation range of the X-rays of which the X-ray dose has been adjusted by the wedge 12b, under the control of the X-ray radiation controlling circuitry 11 (explained later).

The gantry driving circuitry 16 is configured to cause the X-ray generating device 12 and the detector 13 to revolve on the circular orbit centered on the patient P, by driving the rotating frame 15 to rotate.

The detector 13 is a two-dimensional array detector (a planar detector) configured to detect the X-rays that have passed through the patient P. In the detector 13, a plurality of rows of detecting elements are arranged along the body-axis direction of the patient P (i.e., the Z-axis direction in FIG. 2), while each row contains a plurality of X-ray detecting elements corresponding to a plurality of channels. More specifically, the detector 13 according to the first embodiment includes the X-ray detecting elements that are arranged in a large number of rows (e.g., 320 rows) along the body-axis direction of the patient P. For example, the detector 13 is capable of detecting X-rays that have passed through the patient P in a wide range such as a range including the lungs or the heart of the patient P.

The data acquiring circuitry 14 is configured with the DAS and is configured to acquire projection data from X-ray detection data detected by the X-ray detector 13. For example, the data acquiring circuitry 14 generates the projection data by performing an amplifying process, an Analog/Digital (A/D) converting process, a sensitivity correcting process among the channels, and/or the like on X-ray intensity distribution data detected by the detector 13 and further transmits the generated projection data to the console 30 (explained later). For example, when X-rays are continuously emitted from the X-ray tube 12a while the rotating frame 15 is rotating, the data acquiring circuitry 14 acquires a group of projection data corresponding to the entire surrounding (corresponding to 360 degrees). Further, the data acquiring circuitry 14 transmits the acquired pieces of projection data to the console 30 (explained later), while keeping the pieces of projection data in correspondence with the X-ray tube positions. The X-ray tube positions serve as information indicating projection directions of the pieces of projection data. Alternatively, the sensitivity correcting process among the channels may be performed by pre-processing circuitry 34 (explained later).

The couch 20 is a device on which the patient P is placed and includes a couch driving device 21 and a couchtop 22, as illustrated in FIG. 2. The couch driving device 21 is configured to move the patient P into the rotating frame 15 by moving the couchtop 22 in the Z-axis direction. The couchtop 22 is a board on which the patient P is placed.

For example, the gantry 10 performs a helical scan by which the patient P is helically scanned by causing the rotating frame 15 to rotate while the couchtop 22 is being moved. In another example, the gantry 10 performs a conventional scan by which the patient P is scanned on a circular orbit by causing the rotating frame 15 to rotate, while the position of the patient P is being fixed after the couchtop 22 is moved. In yet another example, the gantry 10 implements a step-and-shoot method by which the conventional scan is performed in multiple scan areas, by moving the position of the couchtop 22 at regular intervals.

The console 30 is a device configured to receive operations performed by the operator on the X-ray CT apparatus 1 and also configured to reconstruct X-ray CT image data by using the projection data acquired by the gantry 10. As illustrated in FIG. 2, the console 30 includes input circuitry 31, a display 32, the scan controlling circuitry 33, the pre-processing circuitry 34, storage circuitry 35, image reconstructing circuitry 36, and processing circuitry 37. The pre-processing circuitry 34 and the image reconstructing circuitry 36 are each an example of obtaining circuitry.

The input circuitry 31 includes a mouse, a keyboard, a trackball, a switch, a button, a joystick, and/or the like used by the operator of the X-ray CT apparatus 1 to input various types of instructions and various types of settings. The input circuitry 31 is configured to transfer information about the instructions and the settings received from the operator to the processing circuitry 37. For example, the input circuitry 31 receives, from the operator, an image taking condition for the X-ray CT image data, a reconstructing condition used when the X-ray CT image data is reconstructed, an image processing condition applied to the X-ray CT image data, and the like. Further, the input circuitry 31 also receives an operation to select a medical examination to be performed on the patient P. In addition, the input circuitry 31 receives a designation operation to designate a site rendered in an image.

The display 32 is a monitor referenced by the operator and is configured to display the image data generated from the X-ray CT image data for the operator and to display a Graphical User Interface (GUI) used for receiving the various types of instructions and the various types of settings from the operator via the input circuitry 31, under control of the processing circuitry 37. Further, the display 32 is also configured to display a planning screen for a scan plan and a screen of images during a scan. Further, the display 32 is configured to display a virtual patient image, image data, or the like including X-ray exposure information. The virtual patient image displayed by the display 32 will be explained in detail later.

Under the control of the processing circuitry 37, the scan controlling circuitry 33 is configured to control the projection data acquiring process performed by the gantry 10, by controlling operations of the X-ray radiation controlling circuitry 11, the gantry driving circuitry 16, the data acquiring circuitry 14, and the couch driving device 21. More specifically, the scan controlling circuitry 33 is configured to control projection data acquiring processes during an image taking process to acquire a position determining image (a scanogram image) and during a main image taking process (a scan) to acquire an image used for a diagnosis purpose. In the present example, the X-ray CT apparatus 1 according to the first embodiment is configured so as to be able to take a two-dimensional scanogram image and a three-dimensional scanogram image.

For example, by continuously taking images while moving the couchtop 22 at a constant speed and having the X-ray tube 12a fixed in the position corresponding to 0 degrees (a straight-on position of the patient P), the scan controlling circuitry 33 takes the two-dimensional scanogram image. Alternatively, by intermittently moving the couchtop 22 while the X-ray tube 12a is fixed in the position corresponding to 0 degrees, the scan controlling circuitry 33 may take the two-dimensional scanogram image by repeatedly taking images intermittently in synchronization with the moving of the couchtop. In the present example, the scan controlling circuitry 33 is capable of taking the position determining image, not only from the straight-on direction of the patient P, but also from any arbitrary direction (e.g., a lateral direction).

Further, by acquiring the projection data corresponding to the entire surrounding of the patient P during a scanogram image taking process, the scan controlling circuitry 33 takes the three-dimensional scanogram image. FIG. 3 is a drawing for explaining a three-dimensional scanogram image taking process performed by the scan controlling circuitry 33 according to the first embodiment. For example, as illustrated in FIG. 3, the scan controlling circuitry 33 acquires the projection data corresponding to the entire surrounding of the patient P, by performing either a helical scan or a non-helical scan. In this situation, the scan controlling circuitry 33 performs the helical scan or the non-helical scan on a wide range such as the entire chest, the entire abdomen, the entire upper body, or the entire body of the patient P, by using an X-ray dose smaller than that used in the main image taking process. To perform the non-helical scan, for example, a scan is performed by implementing the step-and-shoot method described above.

When the scan controlling circuitry 33 has acquired the projection data corresponding to the entire surrounding of the patient P in this manner, the image reconstructing circuitry 36 (explained later) is able to reconstruct three-dimensional X-ray CT image data (volume data), and it is therefore possible to generate a position determining image from an arbitrary direction, by using the reconstructed volume data, as illustrated in FIG. 3. In this situation, whether the position determining image is taken two-dimensionally or three-dimensionally may arbitrarily be set by the operator or may be set in advance in accordance with specifics of the medical examination.

Returning to the description of FIG. 2, the pre-processing circuitry 34 is configured to generate corrected projection data by performing a logarithmic converting process as well as correcting processes such as an offset correcting process, a sensitivity correcting process, a beam hardening correcting process, and the like, on the projection data generated by the data acquiring circuitry 14. More specifically, the pre-processing circuitry 34 generates pieces of corrected projection data both for the projection data of the position determining image and for the projection data acquired by performing the main image taking process that were generated by the data acquiring circuitry 14 and further stores the pieces of corrected projection data into the storage circuitry 35.

The storage circuitry 35 is configured to store therein the projection data generated by the pre-processing circuitry 34. More specifically, the storage circuitry 35 stores therein the projection data of the position determining image and the projection data for the diagnosis purpose acquired by performing the main image taking process that were generated by the pre-processing circuitry 34. Further, the storage circuitry 35 is configured to store therein image data generated by the image reconstructing circuitry 36 (explained later), the virtual patient image, and the like. Further, the storage circuitry 35 is configured to store therein a processing result obtained by the processing circuitry 37 (explained later), as appropriate. The virtual patient image and the processing result obtained by the processing circuitry 37 will be explained later.

The image reconstructing circuitry 36 is configured to reconstruct the X-ray CT image data by using the projection data stored in the storage circuitry 35. More specifically, the image reconstructing circuitry 36 reconstructs pieces of X-ray CT image data both from the projection data of the position determining image and the projection data of the image for the diagnosis purpose. In this situation, any of various methods can be used as the reconstructing method. For example, a back projection process may be used. Further, examples of the back projection process include a back projection process using a Filtered Back Projection (FBP) method. Alternatively, the image reconstructing circuitry 36 may reconstruct the X-ray CT image data by using a successive approximation method.

Further, the image reconstructing circuitry 36 is configured to generate image data by performing various types of image processing processes on the X-ray CT image data. After that, the image reconstructing circuitry 36 stores the reconstructed X-ray CT image data and the image data generated by performing the various types of image processing processes, into the storage circuitry 35.

The processing circuitry 37 is configured to exercise overall control of the X-ray CT apparatus 1 by controlling operations of the gantry 10, the couch 20, and the console 30. More specifically, the processing circuitry 37 is configured to control a CT scan performed by the gantry 10, by controlling the scan controlling circuitry 33. Also, the processing circuitry 37 is configured to control the image reconstructing process and the image generating process performed by the console 30, by controlling the image reconstructing circuitry 36. Further, the processing circuitry 37 is configured to exercise control so that the display 32 displays any of the various types image data stored in the storage circuitry 35.

Further, as illustrated in FIG. 2, the processing circuitry 37 is configured to execute a detecting function 37a, a position matching function 37b, and a controlling function 37c. In this situation, for example, processing functions executed by the constituent elements of the processing circuitry 37 illustrated in FIG. 2, namely the functions such as the detecting function 37a, the position matching function 37b, and the controlling function 37c are recorded in the storage circuitry 35 in the form of computer-executable programs. The processing circuitry 37 is a processor configured to realize the functions corresponding to the computer programs (hereinafter, "programs"), by reading the programs from the storage circuitry 35 and executing the read programs. In other words, the processing circuitry 37 that has read the programs has the functions illustrated within the processing circuitry 37 in FIG. 2. The detecting function 37a is an example of detecting circuitry. The controlling function 37c is an example of deriving circuitry and controlling circuitry.

The detecting function 37a is configured to detect each of a plurality of sites of the patient P from the three-dimensional image data. More specifically, the detecting function 37a detects a site such as an organ included in the three-dimensional X-ray CT image data (the volume data) reconstructed by the image reconstructing circuitry 36. For example, with respect to at least one selected from between the volume data of the position determining image and the volume data of the image for the diagnosis purpose, the detecting function 37a detects the site such as an organ on the basis of anatomical feature points called anatomical landmarks. In the present example, the term "anatomical landmark" denotes a point indicating a feature of a site such as a specific bone, organ, blood vessel, nerve, or lumen. In other words, by detecting the anatomical landmark of a specific organ, bone, or the like, the detecting function 37a detects the bone, organ, blood vessel, nerve, lumen, or the like included in the volume data. Further, by detecting the landmark (the feature point) characteristic to human bodies, the detecting function 37a is also capable of detecting the positions of the head, the neck, the chest, the abdomen, the legs, and/or the like included in the volume data. The "sites" used in the description of the present embodiments include any of these positions, in addition to bones, organs, blood vessels, nerves, lumens, and the like. In the following sections, an example of a site detecting process performed by the detecting function 37a will be explained. The "site detecting process" performed by the detecting function 37a may also be referred to as an "AL analysis".

For example, with respect to either the volume data of the position determining image or the volume data of the image for the diagnosis purpose, the detecting function 37a extracts the anatomical landmarks on the basis of voxel values included in the volume data. After that, the detecting function 37a optimizes the positions of the landmarks extracted from the volume data, by eliminating inaccurate landmarks from among the landmarks extracted from the volume data, by comparing the three-dimensional positions of the anatomical landmarks based on information from textbooks and the like, with the positions of the landmarks extracted from the volume data. As a result, the detecting function 37a detects various sites of the patient P included in the volume data. In one example, the detecting function 37a extracts the anatomical landmarks included in the volume data, by using a supervised machine learning algorithm. In the present example, the supervised machine learning algorithm is structured by using a plurality of teacher images in which correct anatomical landmarks are manually arranged. The supervised machine learning algorithm may be configured by using a decision forest, for example.

Further, the detecting function 37a optimizes the extracted landmarks by comparing a model indicating three-dimensional positional relationships among anatomical landmarks of human bodies with the extracted landmarks. In the present example, the model is structured by using the aforementioned teaching images and may be configured by using a point distribution model, for example. In other words, the detecting function 37a optimizes the landmarks by eliminating the inaccurate landmarks, by comparing the model with the extracted landmarks, the model defining the shapes of various sites, the positional relationships thereof, points unique to the sites, and the like on the basis of the plurality of teacher images in which the correct anatomical landmarks are manually arranged.

Figure 4A:
FIG. 4A is a drawing for explaining an example of a site detecting process performed by a detecting function according to the first embodiment.
Figure 4B:
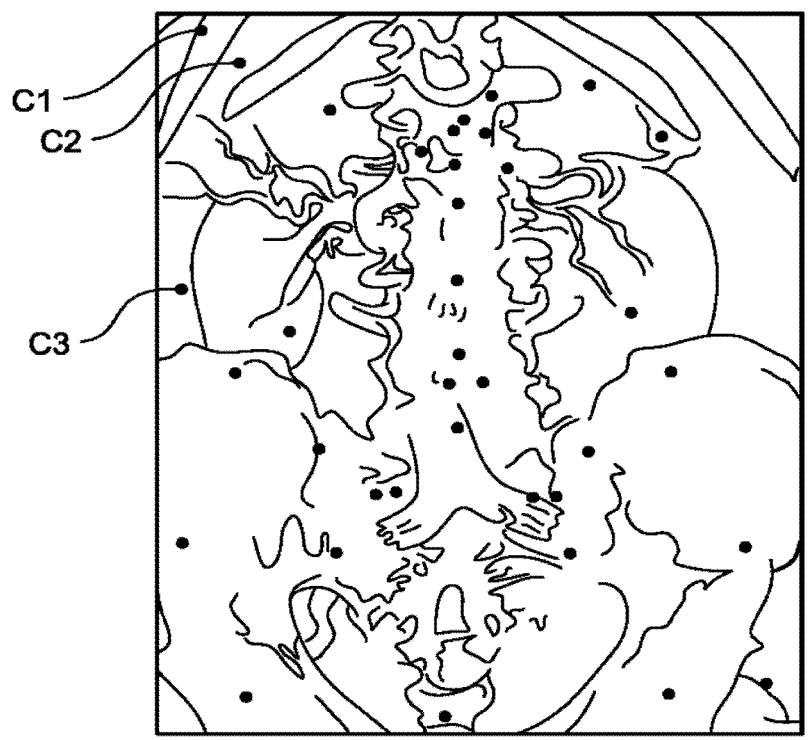
FIG. 4B is another drawing for explaining the example of the site detecting process performed by the detecting function according to the first embodiment.

Next, an example of the site detecting process performed by the detecting function 37a will be explained, with reference to FIGS. 4A, 4B, 5, and 6. FIGS. 4A, 4B, 5, and 6 are drawings for explaining examples of the site detecting process performed by the detecting function 37a according to the first embodiment. Although landmarks are arranged two-dimensionally in FIGS. 4A and 4B, the landmarks are arranged three-dimensionally in actuality. For example, by applying the supervised machine learning algorithm to the volume data, the detecting function 37a extracts voxels regarded as anatomical landmarks (the dots in the drawing), as illustrated in FIG. 4A. Further, by fitting the positions of the extracted voxels to a model defining shapes of various sites, positional relationships thereof, points unique to the sites, and the like, the detecting function 37a extracts only such voxels that correspond to more accurate landmarks, by eliminating inaccurate landmarks from among the extracted voxels, as illustrated in FIG. 4B.

In this situation, the detecting function 37a assigns identification codes for identifying the landmarks indicating the features of the sites, to the extracted landmarks (voxels) and further attaches information in which the identification codes are kept in correspondence with position (coordinates) information of the landmarks to the image data, before storing the image data into the storage circuitry 35. For example, as illustrated in FIG. 4B, the detecting function 37a assigns identification codes such as C1, C2, and C3 to the extracted landmarks (voxels). In this situation, the detecting function 37a attaches an identification code to each of the pieces of data resulting from the detecting process, before storing the pieces of data into the storage circuitry 35. More specifically, the detecting function 37a is configured to detect a site of the patient included in the volume data reconstructed from at least one selected from among: the projection data of the position determining image; projection data acquired in a non-contrast-enhanced state; and projection data acquired while the contrast is enhanced by a contrast agent.

For example, as illustrated in FIG. 5, the detecting function 37a attaches information in which the identification codes are kept in correspondence with the coordinates of the voxels detected from the volume data of the position determining image ("position determining" in the table) to the volume data, before storing the volume data into the storage circuitry 35. In one example, the detecting function 37a extracts the coordinates of landmark points from the volume data of the position determining image and, as illustrated in FIG. 5, stores information such as "identification code: C1, coordinates $(x_1,y_1,z_1)$" and "identification code: C2, coordinates $(x_2,y_2,z_2)$" so as to be kept in correspondence with the volume data. As a result, the detecting function 37a is able to identify what landmarks are present in which positions within the volume data of the position determining image. The detecting function 37a is thus able to detect various sites such as organs on the basis of these pieces of information.

Further, as illustrated in FIG. 5, for example, the detecting function 37a attaches information in which the identification codes are kept in correspondence with the coordinates of the voxels detected from the volume data of the diagnosis-purpose image ("scans" in the table) to the volume data, before storing the volume data into the storage circuitry 35. In this situation, during the scans, the detecting function 37a is able to extract the coordinates of the landmark points from volume data in which the contrast is enhanced by a contrast agent ("contrast-enhanced phase" in the table) and from volume data in which the contrast is not enhanced by a contrast agent ("non-contrast-enhanced phase" in the table), so as to bring the identification codes into correspondence with the extracted coordinates.

In one example, from within the volume data of the diagnosis-purpose image, the detecting function 37a extracts the coordinates of the landmark points from the volume data in the non-contrast-enhanced phase and, as illustrated in FIG. 5, brings information such as "identification code C1, coordinates $(x'_1,y'_1,z'_1)$" and "identification code C2, coordinates $(x'_2,y'_2,z'_2)$" into correspondence with the volume data, before storing the volume data. Further, from within the volume data of the diagnosis-purpose image, the detecting function 37a extracts the coordinates of the landmark points from the volume data in the contrast-enhanced phase and, as illustrated in FIG. 5, brings information such as "identification code C1, coordinates $(x'_1,y'_1,z'_1)$" and "identification code C2, coordinates $(x'_2,y'_2,z'_2)$" into correspondence with the volume data, before storing the volume data. In this situation, when the landmark points are extracted from the volume data in the contrast-enhanced phase, the landmark points include one or more landmark points that became extractable because of the contrast enhancement. For example, when extracting the landmark points from the volume data in the contrast-enhanced phase, the detecting function 37a is able to extract blood vessels and the like of which the contrast was enhanced by the contrast agent. Accordingly, for the volume data in the contrast-enhanced phase, as illustrated in FIG. 5, the detecting function 37a brings identification codes C31, C32, C33, and C34 each of which is used for identifying a different one of the blood vessels, into correspondence with the coordinates such as $(x'_{31}, y'_{31}, z'_{31})$ to $(x'_{34}, y'_{34}, z'_{34})$ of the landmark points represented by the blood vessels and the like that were extracted as a result of the contrast enhancement.

As explained above, the detecting function 37a is able to identify what landmark points are present in which positions within the volume data of the position determining image and of the diagnosis-purpose image. The detecting function 37a is thus able to detect various sites such as organs on the basis of these pieces of information. For example, by using information about an anatomical positional relationship between a target site subject to the detection and other sites positioned in the surroundings of the target site, the detecting function 37a detects the position of the target site. In one example, when the target site is the "lungs", the detecting function 37a obtains coordinate information kept in correspondence with identification codes indicating features of the lungs and further obtains coordinate information kept in correspondence with identification codes indicating sites positioned in the surroundings of the "lungs", such as the "ribs", the "clavicles", the "heart", the "diaphragm", and so on. Further, the detecting function 37a extracts a region of the "lungs" in the volume data by using information about an anatomical positional relationship between the "lungs" and the sites in the surroundings thereof and the obtained coordinate information.

Figure 6:
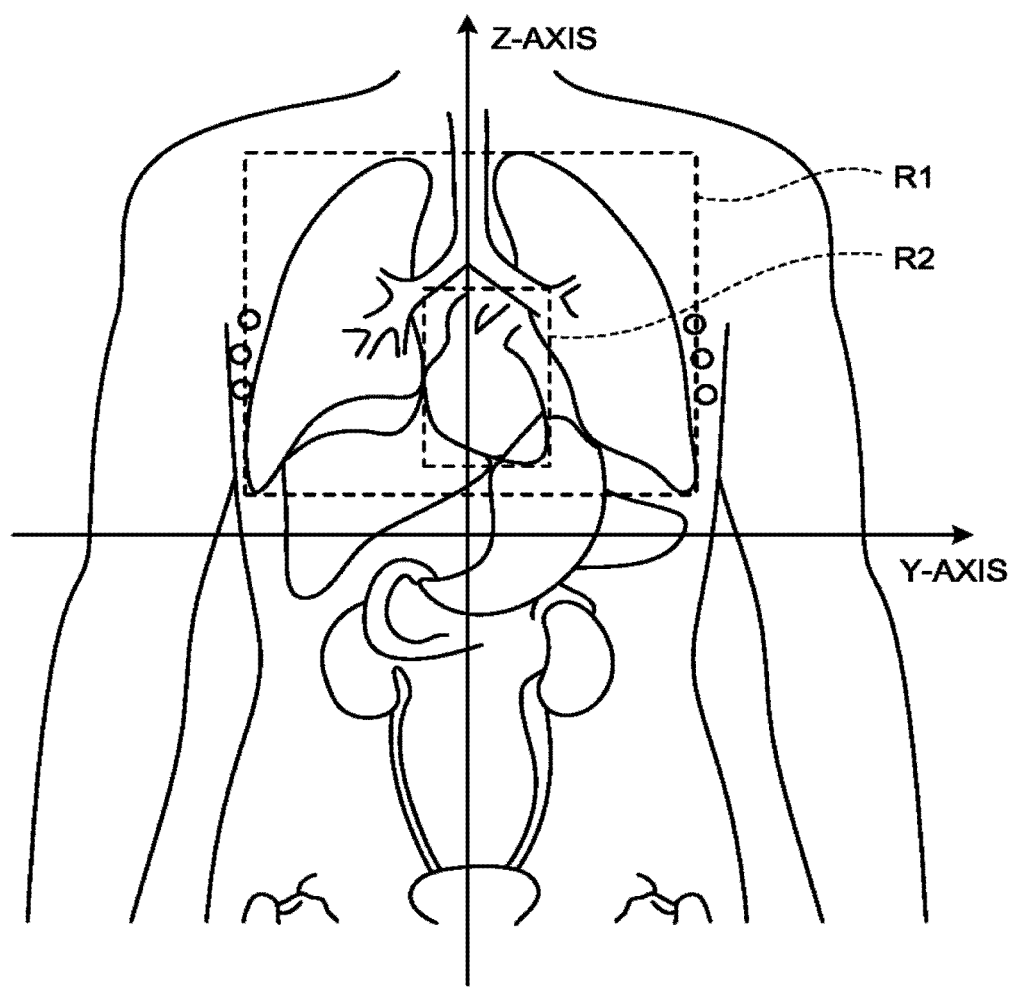
FIG. 6 is yet another drawing for explaining the example of the site detecting process performed by the detecting function according to the first embodiment.

For example, the detecting function 37a extracts a region R1 corresponding to the "lungs" in the volume data, as illustrated in FIG. 6, on the basis of information about positional relationships such as "the lung apices: 2 to 3 cm above the clavicles" and "the lower ends of the lungs: at the height of the seventh ribs", as well as the coordinate information of the sites. In other words, the detecting function 37a extracts the coordinate information of the voxels in the region R1 within the volume data. The detecting function 37a brings the extracted coordinate information into correspondence with site information and further attaches these pieces of information to the volume data, before storing the volume data into the storage circuitry 35. Similarly, as illustrated in FIG. 6, the detecting function 37a is also able to extract a region R2 corresponding to the "heart" in the volume data.

Further, on the basis of landmarks defining the positions of the head and the chest in the human body, the detecting function 37a detects positions included in the volume data. In this situation, it is possible to arbitrarily define the positions of the head, the chest, and the like in the human body. For example, when the region from the seventh cervical vertebra to the lower ends of the lungs are defined as the chest, the detecting function 37a detects a region from a landmark corresponding to the seventh cervical vertebra to a landmark corresponding to the lower ends of the lungs as the chest. In this situation, the detecting function 37a is capable of detecting sites by using other various methods besides the abovementioned method using the anatomical landmarks. For example, the detecting function 37a is capable of detecting the sites included in the volume data by implementing a region growing method based on voxel values, or the like.

The position matching function 37b is configured to match the position of each of the plurality of sites of the patient P included in the three-dimensional image data with the position of each of a plurality of sites in a human body included in virtual patient data. In this situation, the virtual patient data is information indicating a standard position of each of a plurality of sites in the human body. In other words, the position matching function 37b matches the sites of the patient P with the standard positions of the sites and further stores a matching result into the storage circuitry 35. For example, the position matching function 37b matches the virtual patient image in which sites in the human body are arranged in standard positions, with the volume data of the patient P.

Next, the virtual patient image will be explained first. The virtual patient image is generated in advance and stored in the storage circuitry 35 as an image actually taken of a human body by using X-rays, the human body having a standard physique corresponding to a plurality of combinations related to parameters with regard to physiques such as the age, adult/child, male/female, the weight, and the height. In other words, the storage circuitry 35 stores therein data of a plurality of virtual patient images corresponding to the different combinations of the parameters presented above. In this situation, the virtual patient images stored in the storage circuitry 35 are stored while being kept in correspondence with anatomical landmarks (landmarks). For example, the human body has a large number of anatomical landmarks that can be extracted from images relatively easily on the basis of morphological features thereof or the like, by performing an image processing process such as a pattern recognition process. The positions and positional arrangements of the large number of anatomical landmarks in human bodies are roughly fixed depending on physiques corresponding to ages, adult/child, male/female, the weights, and the heights.

Figure 7:
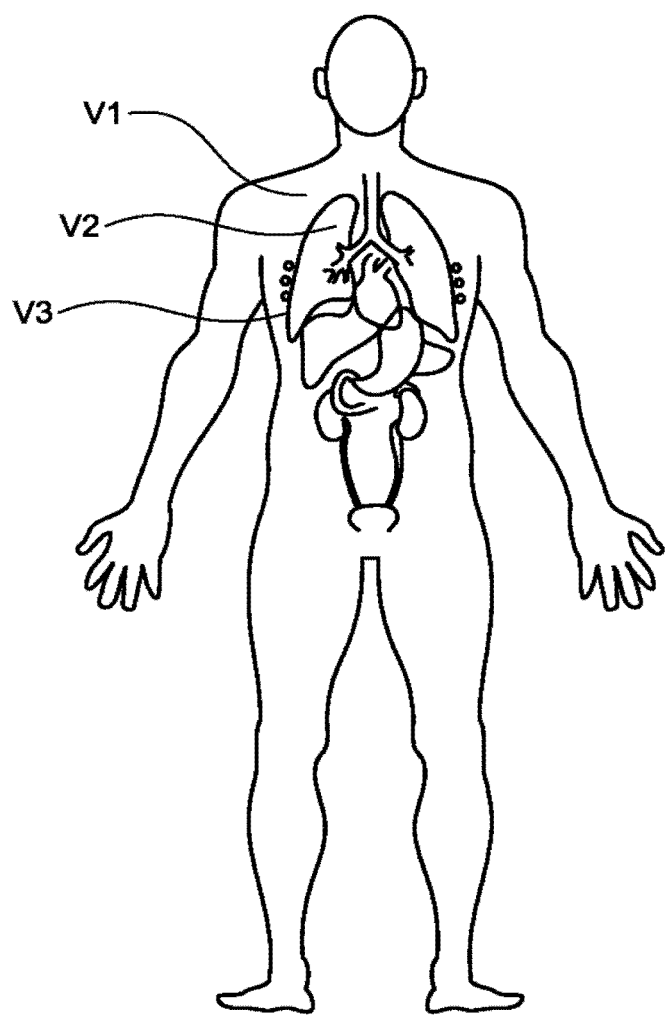
FIG. 7 is a drawing illustrating an example of a virtual patient image stored in storage circuitry according to the first embodiment.

The virtual patient images stored in the storage circuitry 35 are stored after the large number of anatomical landmarks are detected in advance, and position data of the detected landmarks is either attached to or associated with the data of the virtual patient images, together with the respective identification codes of the landmarks. FIG. 7 is a drawing illustrating an example of the virtual patient images stored in the storage circuitry 35 according to the first embodiment. For example, as illustrated in FIG. 7, the storage circuitry 35 stores therein a virtual patient image in which anatomical landmarks and identification codes such as "V1", "V2", "V3", and so on used for identifying the landmarks are kept in association with a three-dimensional human body including sites such as organs.

In other words, the storage circuitry 35 stores therein the coordinates of the landmarks within a coordinate space of a three-dimensional human body image so as to be kept in association with the corresponding identification codes. In one example, the storage circuitry 35 stores therein the coordinates of the corresponding landmark so as to be kept in correspondence with the identification code "V1" illustrated in FIG. 7. Similarly, the storage circuitry 35 stores therein the identification codes and the coordinates of the landmarks so as to be kept in correspondence with one another. Although FIG. 7 illustrates only the lungs, the heart, the liver, the stomach, and the kidneys as organs, the virtual patient image in actuality further includes a large number of organs, bonds, blood vessels, nerves, and the like. Further, although FIG. 7 illustrates only the landmarks corresponding to the identification codes "V1", "V2", and "V3", the virtual patient image in actuality includes a larger number of landmarks.

Figure 8:
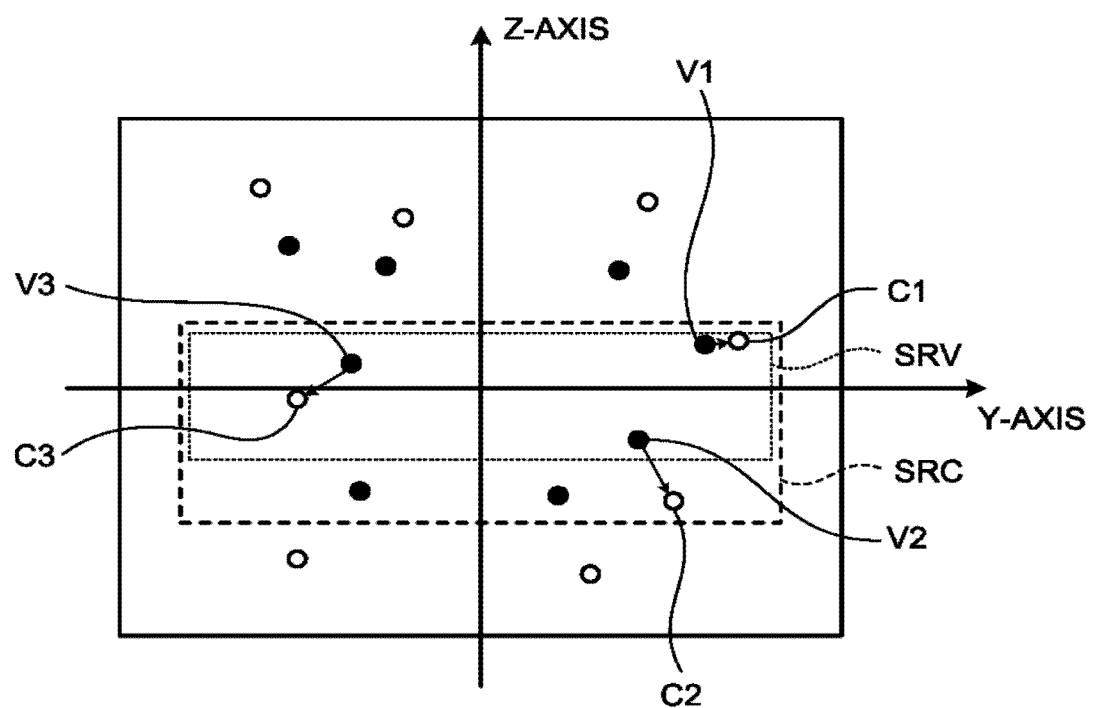
FIG. 8 is a drawing for explaining an example of a matching process performed by a position matching function according to the first embodiment.

The position matching function 37b brings the coordinate space of the volume data into association with the coordinate space of the virtual patient image, by matching the landmarks in the volume data of the patient P detected by the detecting function 37a with the landmarks in the abovementioned virtual patient image, by using the identification codes. FIG. 8 is a drawing for explaining an example of the matching process performed by the position matching function 37b according to the first embodiment. In this situation, FIG. 8 illustrates an example in which the matching process is performed by using three sets of landmarks to which identification codes are assigned so as to indicate mutually the same landmarks between the landmarks detected from a scanogram image and the landmarks detected from the virtual patient image. However, possible embodiments are not limited to this example. It is possible to perform the matching process by using any arbitrary sets of landmarks.

For example, as illustrated in FIG. 8, when matching the landmarks identified with the identification codes "V1", "V2", and "V3" in the virtual patient image, with the landmarks identified with the identification codes "V1", "V2" and "V3" in the scanogram image, the position matching function 37b brings the coordinate spaces of the images in association with each other by performing a coordinate transformation process so as to minimize positional deviations between the pairs of mutually-the-same landmarks. For example, as illustrated in FIG. 8, the position matching function 37b calculates a coordinate transformation matrix "H" presented below, so as to minimize a sum "LS" of positional deviations between "V1 (x1,y1,z1) and C1 (X1,Y1,Z1)", between "V2 (x2,y2,z2) and C2 (X2,Y2,Z2)", and between "V3 (x3,y3,z3) and C3 (X3,Y3,Z3)" that are pairs of anatomically the same landmarks.

$$LS=((X1,Y1,Z1)-H(x1,y1,z1))+((X2,Y2,Z2)-H(x2,y2,z2))+((X3,Y3,Z3)-H(x3,y3,z3))$$

Figure 9:
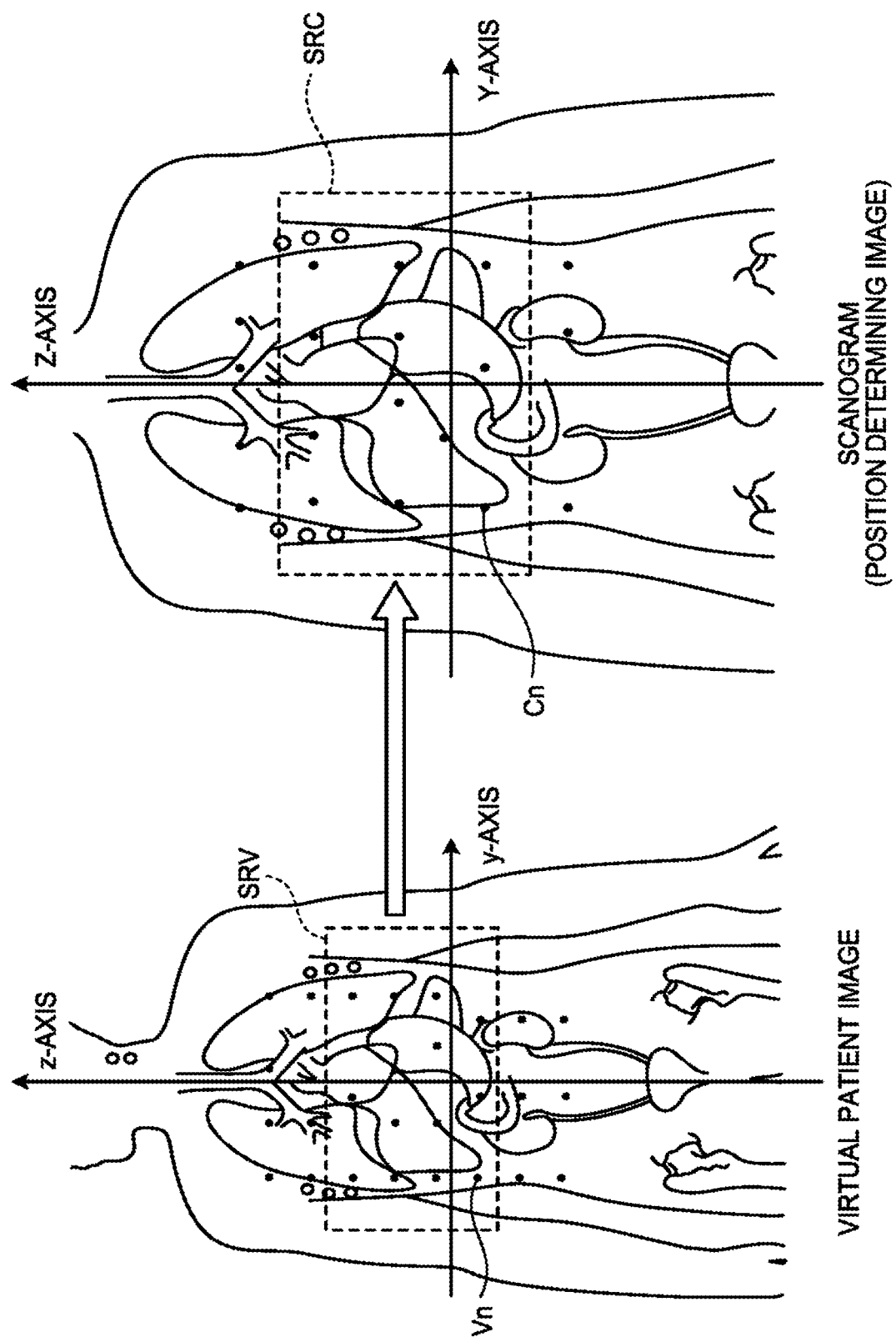
FIG. 9 is a drawing illustrating an example of a scan range transformation process using a coordinate transformation according to the first embodiment.

By using the calculated coordinate transformation matrix "H", the position matching function 37b is able to transform the scan range designated in the virtual patient image into a scan range within the position determining image. For example, by using the coordinate transformation matrix "H", the position matching function 37b is able to transform a scan range "SRV" designated in the virtual patient image into a scan range "SRC" within the position determining image, as illustrated in FIG. 8. FIG. 9 is a drawing illustrating an example of the scan range transformation process using the coordinate transformation according to the first embodiment. For example, as illustrated in the virtual patient image in FIG. 9, when the operator sets the scan range "SRV" in the virtual patient image, the position matching function 37b transforms the set scan range "SRV" into the scan range "SRC" in the scanogram image, by using the coordinate transformation matrix explained above.

As a result, for example, the scan range "SRV" set in the virtual patient image so as to include the landmark corresponding to the identification code "Vn" is set into the scanogram image as being transformed into the scan range "SRC" including the identification code "Cn" corresponding to the same landmark. The coordinate transformation matrix "H" explained above may be stored in the storage circuitry 35 for each patient P so as to be read and used as necessary or may be calculated every time a scanogram image is acquired. As explained herein, according to the first embodiment, by having the virtual patient image displayed for the purpose of designating a range at the time of a pre-set operation and planning a position and a range within the virtual patient image, it is possible to automatically set the position and the range within the position determining image corresponding to the planned position and range by using numerical values, after taking the position determining image (the scanogram image).

Returning to the description of FIG. 2, the controlling function 37c is configured to determine an injection condition for the contrast agent to be administered to the patient P. The controlling function 37c will be explained in detail later.

An overall configuration of the medical information processing system 100 and the exemplary configuration of the X-ray CT apparatus 1 according to the first embodiment have thus been explained. The X-ray CT apparatus 1 according to the first embodiment configured as described above improves the level of precision in setting an image taking position or the like in advance, by transforming either a designated scan position or a designated scan range, on the basis of a matching result between the anatomical landmarks in the virtual patient image, with the landmarks based on structuring members in the patient P within the image data taken by performing either the position determining scan or the contrast-enhanced scan.

In some situations, the X-ray CT apparatus 1 may perform a contrast-enhanced scan by administering a contrast agent to the patient P. In this regard, conventional X-ray CT apparatuses calculate the amount of the contrast agent to be administered, by using the height, the weight, a BMI value, and the like of the patient. The circulation of a contrast agent in the human body is also dependent on the sizes of organs and the amount of blood. For this reason, there are some situations where it may not be possible to accurately calculate an optimal amount of contrast agent by using only those factors such as the height, the weight, and the BMI value.

To cope with those situations, the X-ray CT apparatus 1 according to the first embodiment is configured to detect a structuring member of the patient P and to determine an injection condition for a contrast agent to be administered to the patient P for a contrast-enhanced scan, on the basis of information about the detected structuring member. This function is realized by the controlling function 37c. In the following sections, the controlling function 37c will be explained.

On the basis of the information about the structuring member, the controlling function 37c determines the injection condition for the contrast agent to be administered to the patient P for the contrast-enhanced scan. In this situation, the structuring member is a site to be scanned in the contrast-enhanced scan. For example, as the information about the structuring member, the controlling function 37c derives at least one element selected from among: information about the size of an organ of the patient P, information about the surface area of an organ of the patient P, information about muscle mass of the patient P, information about fat mass of the patient P, and information about skeletal mass of the patient P, and further calculates the amount of the contrast agent to be administered to the patient P as the injection condition. In this situation, from a detection result obtained by the detecting function 37a, the controlling function 37c derives the information about the structuring member in the patient. In other words, by using the detection result obtained by the detecting function 37a, the controlling function 37c derives at least one element selected from among: the information about the size of the organ of the patient P, the information about the surface area of the organ of the patient P, the information about the muscle mass of the patient P, the information about the fat mass of the patient P, and the information about the skeletal mass of the patient P.

More specifically, the controlling function 37c derives the information about the size of the organ of the patient P, by calculating a total number of pixels in the volume data corresponding to the organ of the patient P extracted by the detecting function 37a. Further, the controlling function 37c derives the information about the surface area of the organ of the patient P by calculating a total number of pixels in a surface region (an outline region) in the volume data corresponding to the organ of the patient P extracted by the detecting function 37a. Furthermore, the controlling function 37c derives the information about the skeletal mass of the patient P, by calculating a total number of pixels in the volume data corresponding to the bones of the patient P extracted by the detecting function 37a.

Further, when deriving the information about the muscle mass of the patient P or the information about the fat mass of the patient P, the controlling function 37c performs the following process: The controlling function 37c identifies a region obtained by eliminating the bones, the organs, the blood vessels, the nerves, and the lumens detected by the detecting function 37a from the volume data, as a processing region. After that, the controlling function 37c identifies volume data of a muscle region and volume data of a fat region, on the basis of pixel values (CT values) in the processing region. In this situation, for example, the controlling function 37c identifies, from among the pixels in the processing region, such pixels of each of which the CT value falls in the range from 30 to 50 as pixels in the volume data of the muscle region. Further, for example, the controlling function 37c identifies, from among the pixels in the processing region, such pixels of each of which the CT value falls in the range from −100 to −50 as pixels in the volume data of the fat region. After that, the controlling function 37c derives the information about the muscle mass of the patient P, by calculating the number of pixels in the volume data of the muscle region. Also, the controlling function 37c derives the information about the fat mass of the patient P, by calculating the number of pixels in the volume data of the fat region. In this situation, the controlling function 37c may derive the information about the muscle mass of the patient P and the information about the fat mass of the patient P without using the detection result obtained by the detecting function 37a. In that situation, without identifying the processing region, the controlling function 37c identifies the volume data of the muscle region and the volume data of the fat region from the entirety of the volume data, on the basis of the pixel values (the CT values).

In the following sections, an example will be explained in which information about the size of an organ is derived as the information about a structuring member. Further, in the following sections, an example in which the controlling function 37c has derived the size of the liver will be explained. For example, the controlling function 37c identifies the liver by using a detection result obtained by the detecting function 37a and further derives the size of the liver.

Subsequently, on the basis of the derived size of the liver, the controlling function 37c calculates the amount of the contrast agent to be administered to the patient P for a contrast-enhanced scan. In this situation, the controlling function 37c calculates the amount of the contrast agent by referring to reference information. The reference information will be explained, with reference to FIG. 10. FIG. 10 is a drawing for explaining the first embodiment. As illustrated in FIG. 10, the reference information stores information in which "types of the organ", "sizes of the organ" and "amounts of the contrast agent" are kept in correspondence with one another.

FIG. 10 illustrates an example in which the "types of the organ" are each indicated as the liver. The "sizes of the organ" in FIG. 10 are indicated as ranges of sizes of the organ. For example, under the "sizes of the organ", values such as "X1 to X2", "X2 to X3", and so on are stored. In the present example, X1<X2<X3<X4<X5<X6 is satisfied. Further, the "amounts of the contrast agent" in FIG. 10 indicate different amounts of the contrast agent to be administered depending on the size of the organ. For example, under the "amounts of the contrast agent", values such as "0.90Y (ml)", "Y (ml)", and so on are stored. In one example, the reference information in FIG. 10 derives the amount of the contrast agent as "0.90Y (ml)", when the size of the organ derived by using the detection result obtained by the detecting function 37a falls in the range of "X1 to X2". Although FIG. 10 illustrates an example of the reference information for each type of organ, possible embodiments are not limited to this example. For instance, the X-ray CT apparatus 1 may store therein basic information of each type of organ, in correspondence with either weight values or BMI values of the patient P. Further, with respect to the skeleton mass, the muscle mass, the fat mass, and the body surface area of the patient P, the X-ray CT apparatus 1 also stores therein information in which, similarly, information about each of the structuring members is kept in correspondence with amounts of the contrast agent. Alternatively, the X-ray CT apparatus 1 may store therein the reference information as mathematical functions.

Figure 11:
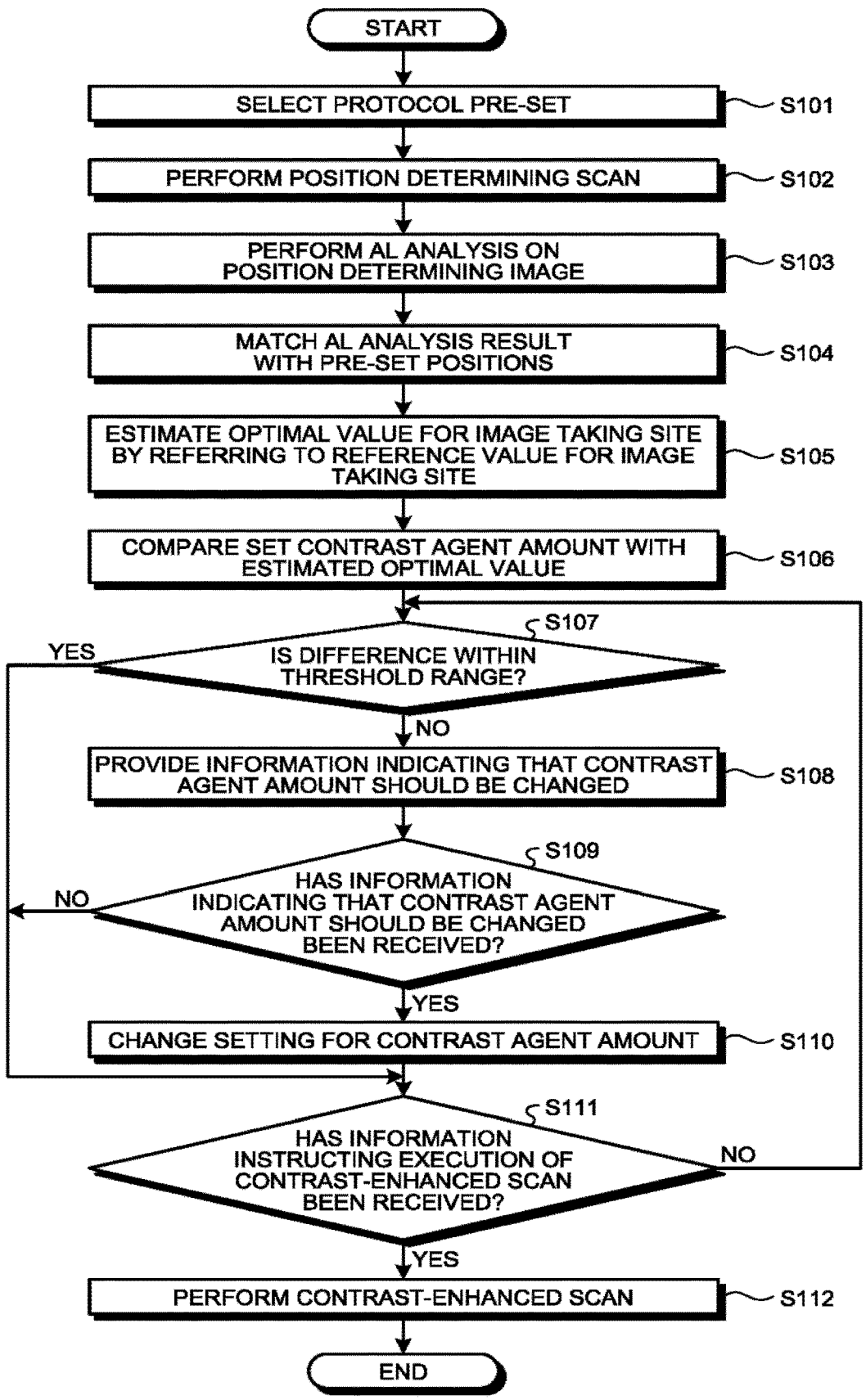
FIG. 11 is a flowchart illustrating a procedure in a process performed by the X-ray CT apparatus according to the first embodiment.

FIG. 11 is a flowchart illustrating a processing procedure performed by the X-ray CT apparatus 1 according to the first embodiment. FIG. 11 illustrates the flowchart for explaining an operation performed by the X-ray CT apparatus 1 as a whole. The following explains which step in the flowchart corresponds to each of the constituent elements.

Step S101 is a step realized by the input circuitry 31. At step S101, the input circuitry 31 receives a selection of a protocol pre-set. Step S102 is a step realized by the scan controlling circuitry 33. At step S102, the scan controlling circuitry 33 performs a position determining scan.

Step S103 is a step corresponding to the detecting function 37a. Step S103 is a step at which the detecting function 37a is realized as a result of the processing circuitry 37 invoking and executing the predetermined program corresponding to the detecting function 37a from the storage circuitry 35. At step S103, the detecting function 37a performs an AL analysis on the position determining image.

Step S104 is a step corresponding to the position matching function 37b. Step S104 is a step at which the position matching function 37b is realized as a result of the processing circuitry 37 invoking and executing the predetermined program corresponding to the position matching function 37b from the storage circuitry 35. At step S104, the position matching function 37b matches a result of the AL analysis with pre-set positions.

Steps S105 through S110 are steps corresponding to the controlling function 37c. Steps S105 through S110 are steps in which the controlling function 37c is realized as a result of the processing circuitry 37 invoking and executing the predetermined program corresponding to the controlling function 37c from the storage circuitry 35. At step S105, the controlling function 37c estimates an optimal value for the amount of the contrast agent for the image taking site, by referring to a reference value corresponding to the image taking site. For example, the controlling function 37c detects a structuring member of the patient P and further determines an injection condition for the contrast agent to be administered to the patient P for a contrast-enhanced scan, on the basis of the information about the detected structuring member.

After that, at step S106, the controlling function 37c compares a set contrast agent amount with the estimated optimal value for the amount of the contrast agent. Subsequently, at step S107, the controlling function 37c judges whether or not the difference between the set contrast agent amount and the estimated optimal value for the amount of the contrast agent is within a threshold range. In this situation, when the controlling function 37c has determined that the difference between the set contrast agent amount and the estimated optimal value for the amount of the contrast agent is within the threshold range (step S107: Yes), the process proceeds to step S111. On the contrary, when the controlling function 37c has determined that the difference between the set contrast agent amount and the estimated optimal value for the amount of the contrast agent is not within the threshold range (step S107: No), information is provided at step S108 to indicate that the amount of the contrast agent should be changed. In other words, when having determined that the difference between the set contrast agent amount and the estimated optimal value for the amount of the contrast agent is not within the threshold range, the controlling function 37c determines that the determined injection condition is different from the injection condition that was set in advance. Further, the controlling function 37c informs the operator that the determined injection condition is different from the injection condition that was set in advance.

After that, at step S109, the controlling function 37c judges whether information indicating that the amount of the contrast agent should be changed has been received. In this situation, when the controlling function 37c has determined that no information indicating a change in the amount of the contrast agent has been received (step S109: No), the process proceeds to step S111. On the contrary, when the controlling function 37c has determined that information indicating a change in the amount of the contrast agent has been received (step S109: Yes), the controlling function 37c updates the setting for the amount of the contrast agent at step S110. For example, when having received information from the operator indicating that the injection condition that was set in advance should be changed to the determined injection condition, the controlling function 37c configures the determined injection condition into the contrast agent injector.

Step S111 is a step realized by the scan controlling circuitry 33. At step S111, the scan controlling circuitry 33 judges whether or not information instructing execution of a contrast-enhanced scan has been received. In this situation, when the scan controlling circuitry 33 has determined that no information instructing execution of a contrast-enhanced scan has been received (step S111: No), the process proceeds to step S107. On the contrary, when the scan controlling circuitry 33 has determined that information instructing execution of a contrast-enhanced scan has been received (step S111: Yes), a contrast-enhanced scan is performed at step S112.

As explained above, according to the first embodiment, the injection condition for the contrast agent to be administered to the patient P for the contrast-enhanced scan is determined, on the basis of the information about the structuring member. For example, even when the weight of the patient P is heavy, the X-ray CT apparatus 1 according to the first embodiment makes the amount of the contrast agent smaller than the reference value, when the site of which the contrast is to be enhanced is the liver, while the size of the liver of the patient P is smaller than the reference value. Conversely, even when the weight of the patient P is light, the X-ray CT apparatus 1 according to the first embodiment makes the amount of the contrast agent larger than the reference value, when the site of which the contrast is to be enhanced is the liver, while the size of the liver of the patient P is larger than the reference value. As another example, even when the physique of the patient P is large, the X-ray CT apparatus 1 according to the first embodiment decreases the amount of the contrast agent when the muscle mass is small while the fat mass is large and increases the amount of the contrast agent when the skeleton mass is large while the muscle mass is large. With these arrangements, the operator is able to accurately determine the amount of the contrast agent to be administered to the patient P. As a result, according to the first embodiment, it is possible to aid the viewer to interpret the image having high contrast, with a high level of precision.

In addition, as a result, according to the first embodiment, while aiding the viewer to interpret the images with a high level of precision, it is also possible to suppress the amount of the contrast agent to be administered to the patient to a minimum necessary level. Consequently, it is possible to reduce burdens on the patient.

In the first embodiment above, the example is explained in which the controlling function 37c is configured to inform the operator that the determined injection condition is different from the injection condition that was set in advance and to further configure the determined injection condition into the contrast agent injector when having received the information from the operator indicating that the injection condition that was set in advance should be changed to the determined injection condition. However, possible embodiments are not limited to this example. For instance, the controlling function 37c may configure the determined injection condition into the contrast agent injector, without informing the operator that the determined injection condition is different from the injection condition that was set in advance or without receiving the information from the operator indicating the change.

Second Embodiment

In the first embodiment, the example is explained in which one element is derived as the information about a structuring member, and the amount of the contrast agent to be administered to the patient is calculated as the injection condition. In this regard, the number of elements derived as the information about structuring members may be two or more. Thus, in a second embodiment, an example will be explained in which two or more elements are used as the information about the structuring members.

A configuration of an X-ray CT apparatus according to the second embodiment is almost the same as the configuration of the X-ray CT apparatus 1 according to the first embodiment, except that a part of the functions of the controlling function 37c is different. Thus, the explanation about configurations other than the controlling function 37c will be omitted. When using a plurality of elements, the controlling function 37c is configured to calculate a statistical value for the amount of the contrast agent to be administered to the patient calculated for each of the plurality of elements, as the amount of the contrast agent to be administered to the patient. FIG. 12 is a drawing for explaining a second embodiment.

FIG. 12 illustrates an example in which "skeleton mass", "muscle mass", and "the size of the organ" are derived as the information about structuring members, so that an amount of contrast agent is calculated for each of the derived elements. For example, on the basis of the derived "skeleton mass", the controlling function 37c calculates an amount of contrast agent as "1.10Y (ml)". On the basis of the derived "muscle mass", the controlling function 37c calculates an amount of contrast agent as "0.90Y (ml)". On the basis of the derived "size of the organ", the controlling function 37c calculates an amount of contrast agent as "0.90Y (ml)". Subsequently, the controlling function 37c calculates a statistical value for the calculated amounts of the contrast agent to be administered to the patient P. For example, the controlling function 37c calculates an average value of the amounts of the contrast agent as the amount of the contrast agent to be administered to the patient P. In the example in FIG. 12, the controlling function 37c calculates the amount of the contrast agent to be administered as "0.97Y (ml)". The controlling function 37c may calculate an average value after applying weights to the elements.

As explained above, according to the second embodiment, the X-ray CT apparatus 1 calculates the amount of the contrast agent to be administered to the patient P, by using the plurality of elements as the information about the structuring members. With this arrangement, according to the second embodiment, it is possible to more accurately determine the injection condition for the contrast agent to be administered to the patient P.

In the second embodiment also, the example is explained in which the controlling function 37c is configured to inform the operator that the determined injection condition is different from the injection condition that was set in advance and to further configure the determined injection condition into the contrast agent injector when having received the information from the operator indicating that the injection condition that was set in advance should be changed to the determined injection condition. However, possible embodiments are not limited to this example. For instance, the controlling function 37c may configure the determined injection condition into the contrast agent injector, without informing the operator that the determined injection condition is different from the injection condition that was set in advance or without receiving the information from the operator indicating the change.

Third Embodiment

In the first and the second embodiments above, the controlling function 37c is configured to determine the amount of the contrast agent, on the basis of the information about the one or more structuring members. However, there are some situations where, when the speed of the blood flow is high, it is not possible to enhance the contrast of a target subject to the contrast enhancement even with the injection of a contrast agent. To cope with these situations, an example will be explained in a third embodiment in which at least one selected from between the concentration and the injection speed of the contrast agent to be administered to the patient is calculated as an injection condition.

A configuration of an X-ray CT apparatus according to the third embodiment is almost the same as the configuration of the X-ray CT apparatus 1 according to the first embodiment, except that a part of the functions of the controlling function 37c is different. Thus, the explanation about configurations other than the controlling function 37c will be omitted.

For example, the controlling function 37c according to the third embodiment is configured to calculate, as an injection condition, at least one selected from between the concentration and the injection speed of the contrast agent to be administered to the patient P, on the basis of a scan condition and information about the size of the heart derived as information about a structuring member. In this situation, for example, the controlling function 37c calculates the speed of the blood flow by deriving a cardiac ejection amount by performing a helical scan so as to include various states corresponding to mutually-different cardiac phases. After that, for example, when the degree of contrast enhancement is not sufficient for the organ subject to a contrast enhancement, the controlling function 37c displays a comment in a pop-up window indicating that the concentration of the contrast agent should be increased or that the injection speed should be raised, so that the contrast agent is injected at the same speed as the speed of the blood flow. After that, when having received information from the operator indicating that the injection condition should be changed, the controlling function 37c increases the concentration of the contrast agent or raises the injection speed. Alternatively, the controlling function 37c may be configured to calculate the cardiac ejection amount from systolic and diastolic blood pressure values. With these arrangements, according to the third embodiment, it is possible to generate a reconstructed image having clear contrast, even when the speed of the blood flow is high.

OTHER EMBODIMENTS

The first to the third embodiments have thus been explained. It is, however, possible to carry out the present disclosure in various different forms other than those described in the first to the third embodiments above.

The controlling function 37c may be configured to obtain information indicating sensitivity of the patient P to contrast agents and to determine an injection condition for the contrast agent to be administered to the patient P by referring to the obtained information. For example, the controlling function 37c obtains, from the HIS, information indicating whether or not the patient is allergic to contrast agents and kidney function information such as a creatine level in the blood or the like. Further, when the patient P is allergic to contrast agents or when the creatine value is equal to or larger than a predetermined threshold value, the controlling function 37c alerts the operator. FIG. 13 is a drawing for explaining this other embodiment.

FIG. 13 illustrates an example in which the patient P is allergic to contrast agents. For example, to alert the operator, the controlling function 37c displays in a pop-up window a message reading "<Caution> The patient is allergic to contrast agents". Further, when having alerted the operator, the controlling function 37c may stop the contrast agent injector from injecting the contrast agent. Alternatively, when having alerted the operator and having received an instruction from the operator to perform a contrast-enhanced image taking process, the controlling function 37c may limit the amount of the contrast agent so as to be injected only up to a predetermined volume set in advance.

Further, the controlling function 37c may be configured to request a medical doctor in charge to approve of changing the injection condition for the contrast agent. For example, the controlling function 37c generates an e-mail requesting an approval for a change in the injection condition for the contrast agent and sends the e-mail to the medical doctor in charge. Alternatively, the controlling function 37c may contact the medical doctor in charge via an intra-hospital telephone line or the like to request an approval for a change in the injection condition for the contrast agent. In those situations, when having received an approval from the medical doctor in charge, the controlling function 37c changes the injection condition for the contrast agent. In other words, the controlling function 37c does not change the amount of the contrast agent configured in the contrast agent injector, until the controlling function 37c receives an approval from the medical doctor in charge.

Further, as a result of the AL analysis, when the patient has only one kidney or only one lung or when the information about the size of an organ exhibits a value equal to or smaller than a predetermined reference value, there is a difference between the patient and the standard human body model. In that situation, the controlling function 37c suppresses the injection condition for the contrast agent to be administered to the patient P so as to be smaller than a predetermined threshold value. In other words, the controlling function 37c derives information about the size of the organ as the information about the structuring member, and either when the information about the size of the organ exhibits a value equal to or smaller than the predetermined reference value or when at least a part of the organ is missing, the controlling function 37c suppresses the injection condition for the contrast agent to be administered to the patient P so as to be smaller than the predetermined threshold value. In addition, the X-ray CT apparatus 1 displays information indicating that the organ is missing in the image of the virtual patient in a recognizable manner. For example, the X-ray CT apparatus 1 may display the missing organ by filling the area with solid color or may add an annotation.

Further, when the determined injection condition has been used in a contrast-enhanced scan, the controlling function 37c may be configured to store the injection condition into a predetermined storage unit. For example, the X-ray CT apparatus 1 stores the injection condition for the contrast agent into the HIS or the RIS. Further, the X-ray CT apparatus 1 uses the injection condition for the contrast agent when performing an image taking process next time. Further, the X-ray CT apparatus 1 may output the determined injection condition to an external apparatus.

In the embodiments described above, the example is explained in which the detecting function 37a is configured to perform the AL analysis by using either the volume data of the position determining image or the volume data of the diagnosis-purpose image. However, possible embodiments are not limited to this example. For instance, the detecting function 37a may be configured to perform the AL analysis by using a two-dimensional position determining image. Further, the detecting function 37a may be configured to perform the AL analysis by using images that were taken in the past by the apparatus of its own for the purpose of diagnosing the same patient. Alternatively, the detecting function 37a may be configured to perform the AL analysis by using medical image data of the same patient that was taken by another apparatus.

Further, in the embodiments above, the X-ray CT apparatus is explained as an example of a medical image taking apparatus; however, possible embodiments are not limited to this example. For instance, the medical image taking apparatus may be an X-ray diagnosis apparatus, an ultrasound diagnosis apparatus, a Magnetic Resonance Imaging (MRI) apparatus, or the like.

Further, in the embodiments above, the example is explained in which the medical image taking apparatus performs the process of determining the injection condition for the contrast agent to be administered to the patient P; however, possible embodiments are not limited to this example. For instance, it is acceptable to provide a medical image processing apparatus or the like as a management apparatus, so that the management apparatus performs the process of determining the injection condition for the contrast agent to be administered to the patient P. In other words, the management apparatus is configured to obtain image data of the patient. Further, the management apparatus is configured to detect each of a plurality of sites of the patient from the image data. Further, the management apparatus is configured to subsequently derive information about a structuring member in the patient on the basis of the detection result. Further, the management apparatus is configured to determine the injection condition for the contrast agent to be administered to the patient for a contrast-enhanced scan, on the basis of the information about the structuring member.

The term "processor" used in the explanation above denotes, for example, a circuit such as a Central Processing Unit (CPU), a Graphics Processing Unit (GPU), an Application Specific Integrated Circuit (ASIC), or a programmable logic device (e.g., a Simple Programmable Logic Device [SPLD], a Complex Programmable Logic Device [CPLD], or a Field Programmable Gate Array [FPGA]). Each of the processors realizes the function thereof by reading a program stored in the storage circuit and executing the read program. Alternatively, it is also acceptable to directly incorporate the program into the circuit of each of the processors, instead of having the programs stored in the storage circuit. In that situation, each of the processors realizes the function thereof by reading the program incorporated in the circuit thereof and executing the read program. The processors according to the present embodiments each do not necessarily have to individually be configured as a single circuit. It is also acceptable to structure a single processor by combining together a plurality of independent circuits so as to realize the functions thereof. Further, it is also acceptable to integrate the plurality of constituent elements illustrated in FIG. 2 into a single processor so as to realize the functions thereof.

The constituent elements of the apparatuses and the devices illustrated in the drawings in the embodiments above are based on functional concepts. Thus, it is not necessary to physically configure the constituent elements as indicated in the drawings. In other words, the specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a computer program analyzed and executed by the CPU or may be realized as hardware using wired logic.

Further, it is possible to realize the controlling method explained in the first embodiment, by causing a computer such as a personal computer or a workstation to execute a control computer program (hereinafter, "control program") prepared in advance. It is possible to distribute the control program via a network such as the Internet. Further, the control program may be executed as being recorded on a computer-readable recording medium such as a hard disk, a flexible disk (FD), a Compact Disk Read-Only Memory (CD-ROM), a Magneto-Optical (MO) disk, a Digital Versatile Disk (DVD), or the like and being read from the recording medium by a computer.

As explained above, according to at least one aspect of the embodiments, it is possible to accurately determine the injection condition for the contrast agent to be administered to the patient.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis apparatus comprising:
obtaining circuitry configured to obtain volume image data of a patient;
detecting circuitry configured to detect each of a plurality of sites of the patient from the volume image data; and
processing circuitry configured to:
derive, on a basis of a detection result obtained by the detecting circuitry, information about a structuring member in the patient by deriving a plurality of elements selected from: a total number of pixels included in an organ of the patient in the volume image data corresponding a three-dimensional size of the organ; a total number of pixels in a surface region of the volume image data corresponding to a surface area of the organ of the patient; a number of pixels in the volume image data corresponding to a muscle mass of the patient; a number of pixels in the volume image data corresponding to a fat mass of the patient; and a total number of pixels in the volume image data corresponding to a skeleton mass of the patient;
calculate a statistical value using each of the derived plurality of elements; and
determine an amount of contrast agent to be administered to the patient for a contrast-enhanced scan, on a basis of the statistical value.

2. The medical image diagnosis apparatus according to claim 1, wherein the structuring member is a site to be scanned in the contrast-enhanced scan.

3. The medical image diagnosis apparatus according to claim 1, wherein the processing circuitry further calculates at least one selected from between a concentration and an injection speed of the contrast agent to be administered to the patient, on a basis of a scan condition and information about a size of a heart.

4. The medical image diagnosis apparatus according to claim 1, wherein the processing circuitry obtains information indicating sensitivity of the patient to contrast agents and determines the amount of contrast agent to be administered to the patient by referring to the obtained information.

5. The medical image diagnosis apparatus according to claim 1, wherein the processing circuitry derives the total number of pixels included in the organ in the volume image data corresponding to the three-dimensional size of the organ as the information about the structuring member, and either when the total number of pixels included in the organ in the volume image data corresponding to the three-dimensional size of the organ exhibits a value equal to or smaller than a predetermined reference value or when at least a part of the organ is missing, the processing circuitry determines the amount of contrast agent to be administered to the patient so as to be smaller than a predetermined threshold value.

6. The medical image diagnosis apparatus according to claim 1, wherein the processing circuitry configures the determined amount of contrast agent into a contrast agent injector.

7. The medical image diagnosis apparatus according to claim 1, wherein, when the determined amount of contrast agent is different from an amount of contrast agent that was set in advance, the processing circuitry further informs an operator.

8. The medical image diagnosis apparatus according to claim 7, wherein, when having received information from the operator indicating that the injection condition that was set in advance should be changed to the determined amount of contrast agent, the processing circuitry configures the determined amount of contrast agent into a contrast agent injector.

9. The medical image diagnosis apparatus according to claim 1, wherein, when the determined amount of contrast agent has been used in the contrast-enhanced scan, the processing circuitry stores the determined amount of contrast agent into a storage circuitry.

10. The medical image diagnosis apparatus according to claim 1, wherein the processing circuitry is configured to derive pixel values corresponding to the muscle mass or the fat mass of the patient by:
determining a first image region,
eliminating at least one of bones, organs, blood vessels, nerves, and lumens from the first image region to produce a second image region, and
identifying volume data of muscles or fat on a basis of pixel values from the second image region.

11. The medical image diagnosis apparatus according to claim 1, wherein the determined amount of contrast agent comprises an administration amount of the contrast agent.

12. A management apparatus comprising:
obtaining circuitry configured to obtain volume image data of a patient;
detecting circuitry configured to detect each of a plurality of sites of the patient from the volume image data; and
processing circuitry configured to:
derive, on a basis of a detection result obtained by the detecting circuitry, information about a structuring member in the patient by deriving a plurality of elements selected from: a total number of pixels included in an organ of the patient in the volume image data corresponding a three-dimensional size of the organ; a total number of pixels in a surface region of the volume image data corresponding to a surface area of the organ of the patient; a number of pixels in the volume image data corresponding to a muscle mass of the patient; a number of pixels in the volume image data corresponding to a fat mass of the patient; and a total number of pixels in the volume image data corresponding to a skeleton mass of the patient;
calculate a statistical value using each of the derived plurality of elements; and
determine an injection condition for a contrast agent to be administered to the patient for a contrast-enhanced scan, on a basis of the statistical value.

13. The management apparatus according to claim 12, wherein the processing circuitry is configured to derive pixel values corresponding to the muscle mass or the fat mass of the patient by:
determining a first image region,
eliminating at least one of hones, organs, blood vessels, nerves, and lumens from the first image region to produce a second image region, and
identifying volume data of muscles or fat on a basis of pixel values from the second image region.

14. The management apparatus according to claim 12, wherein the determined injection condition comprises an administration amount of the contrast agent.

\* \* \* \* \*